United States Patent
Shaw

[11] Patent Number: 5,765,305
[45] Date of Patent: Jun. 16, 1998

[54] METHOD OF INCREASING THE SIZE OF A ROSE HEAD DURING GROWTH

[76] Inventor: Kenneth P. Shaw, 570 N. Island Dr., Golden Beach, Fla. 33179

[21] Appl. No.: 585,952

[22] Filed: Jan. 16, 1996

[51] Int. Cl.[6] .............. A01G 9/00; A01G 9/12; A01G 5/06; A01H 3/00
[52] U.S. Cl. ............. 47/58; 47/41.1; 800/DIG. 36
[58] Field of Search ........... 47/58, 41.01; 800/DIG. 36

[56] References Cited

U.S. PATENT DOCUMENTS

| | | | |
|---|---|---|---|
| 3,917,889 | 11/1975 | Gaffney et al. | 428/36 |
| 3,998,006 | 12/1976 | Riedel | 47/9 |
| 4,016,678 | 4/1977 | Larsen | 47/77 |
| 4,082,831 | 4/1978 | Hase | 264/249 |
| 4,091,925 | 5/1978 | Griffo et al. | 206/423 |
| 5,135,771 | 8/1992 | Chackal | 427/4 |

FOREIGN PATENT DOCUMENTS 3-290116  12/1991  Japan .................. A01G 5/06

OTHER PUBLICATIONS

Biran et al. Effects of varying light intensities and temperature treatments applied to whole plants, or locally to leaves of flower buds, on growth and pigmentation of 'Baccara' roses. Physiologia Plantarum. vol 31. pp. 175–179, 1974.

*Primary Examiner*—David T. Fox
*Assistant Examiner*—Melissa L. Kimball
*Attorney, Agent, or Firm*—Anthony R. Barkume, P.C.

[57] ABSTRACT

The present invention is a method for increasing the size of a rose head prior to cutting the rose head from its plant comprising at least partially preventing the rose head from opening prior to cutting the rose head from the plant. This is accomplished by constricting the rose head with an elastic material wrapped around the rose head. The elastic material is preferably a netting sleeve having at least one open end suitable for placing over the rose head, the netting sleeve being comprised of an elastic netting material such as nylon or rubber capable of stretching so as to fit snugly over the rose head. In particular, the rose head is at least partially constricted for a predetermined time period prior to cutting from the plant. By partially constricting the rose head from opening, the amount of light and thus heat incident on inner petals of the rose head is reduced and the growth rate is accordingly increased, which results is a larger rose head heretofore unobtainable without allowing the outer petals of the rose head to commence opening.

8 Claims, 2 Drawing Sheets

METHOD OF INCREASING THE SIZE OF A ROSE HEAD DURING GROWTH

BACKGROUND OF THE INVENTION

The present invention relates to a method for increasing the size of a rose head prior to cutting the rose head from the stem, and in particular to a method of at least partially preventing the rose head from opening by placing an elastic constraining material on and around the rose head for a predetermined time prior to cutting the rose head from the stem in order to effect such increased head growth without suffering loss of shelf life of the rose after cutting.

Roses are grown by commercial rose growers and cut from the plant for the purpose of vending the cut roses to consumers via commercial channels such as distributors and retail flower shops. Roses with larger heads have more commercial value than those with smaller heads; it has thus been desired to increase the size of the rose head prior to vending to the consumer. Typically, a rose grower will cut the rose stem from the plant and ship the cut rose at a certain time in its growth stage for marketing. The optimum time to cut the rose stem is when the rose head has reached as large a size as possible without substantial opening of the petals.

If a rose stem is cut prior to the optimum time, then the size of the rose head will be small and the rose will be less valuable. In addition, the petals of the rose head will be too tight and the rose will not open, thus making the rose unmarketable. However, the life expectancy of the rose after cutting is generally longer when the petals are tighter, so a rose cut prior to the optimum time will last longer than one cut later in its growth stage. On the other hand, if the rose stem is cut too long after the optimum time, then the petals will be already open (some may even fall off) and the flower will have a shorter life expectancy and thus be less valuable.

There is therefore a long felt need in the art to increase the size of the rose head prior to cutting the stem without the rose head opening and losing petals prematurely.

SUMMARY OF THE INVENTION

The present invention is a method for increasing the size of a rose head prior to cutting the rose head from its plant comprising at least partially preventing the rose head from opening prior to cutting the rose head from the plant. This is accomplished by constricting the opening of the rose head with an elastic material wrapped around the rose head. The elastic material is preferably a netting sleeve having at least one open end suitable for placing over the rose head, the netting sleeve being comprised of an elastic netting material such as nylon or rubber capable of stretching so as to fit snugly over the rose head. In particular, the rose head is at least partially constricted for a predetermined time period prior to cutting from the plant.

By constricting the rose head from opening, the amount of light (and thus heat) incident on the inner petals of the rose head is reduced and the growth rate of the rose head is accordingly increased, which results is a larger rose head heretofore unobtainable without allowing the outer petals of the rose head to commence opening.

DETAILED DESCRIPTION OF THE PREFERRED EMBODIMENT

Figure 1:
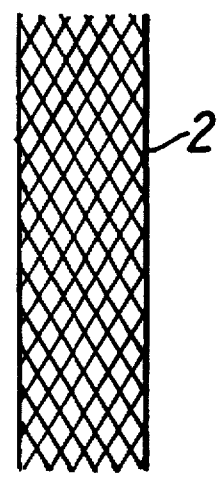
FIG. 1 is an illustration of the nylon netting sleeve used in the preferred embodiment in order to effect increased rose head growth.

A sleeve of nylon netting 2 as shown in FIG. 1 is utilized in accordance with the preferred embodiment of the present invention. The netting sleeve 2 is formed so as to be able to stretch and conform to the rose head when the rose head is in its final growth stages, which is prior to normal cutting of the stem. Preferably, the netting 2 in its quiescent, unstretched stage will be smaller then the rose head but will easily expand so as to fit snugly over the rose head when desired. For example, the nylon netting 2 used in the preferred embodiment can stretch to a distance of six times its unstretched width. Due to the resiliency of the nylon netting, the sleeve will hold itself around the rose head until it is desired to be removed.

Figure 2:
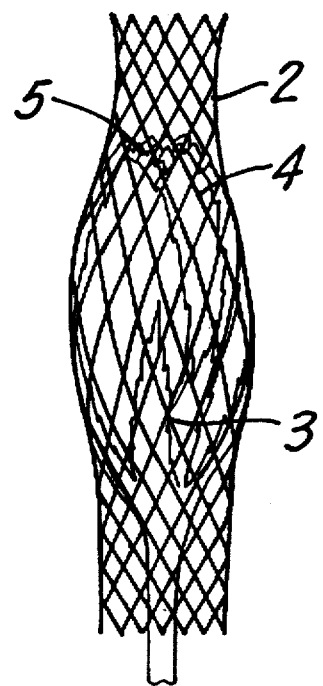
FIG. 2 is an illustration of a rose head covered with the netting sleeve of FIG. 1 in accordance with the preferred embodiment of the present invention.

To effect the increased rose head size of the present invention, the netting sleeve 2 is placed over the rose head 3 as shown in FIG. 2 so as to conform snugly to the surface thereof. The placement of the netting sleeve should occur a few days prior to the expected cutting time of the rose head as will be explained further below.

The placement of the nylon netting sleeve 2 over the rose head 3 prior to cutting the stem from the plant performs two interrelated functions which the applicant has determined are critical to the present invention. First, the netting sleeve 2 acts to physically constrict the opening of the rose head 3, thus helping in keeping intact the outer or guard petals 4 of the rose. The guard petals 4 would normally protect the remainder of the rose head (i.e., the inner petals 5) during shipping and handling, and often would fall off as a result of handling of the cut plant. However, by placing the netting sleeve around the rose head prior to cutting, it has been determined that the rose head 3 is slightly constricted from opening at the normal time, and the guard petals 4 retain a stronger natural bond with the rose head 3 as a result thereof. Since the guard petals 4 retain a stronger bond, they do not fall off as easily during handling as they would otherwise. Moreover, the overall tightness of the rose head 3 is increased by the slight constriction effect of the netting sleeve 2, thus acting to counteract the otherwise decreased shelf life of a larger rose head. The head also has more petals due to the presence of guard petals 4. Without the net, two to three outer petals 4 would be lost and the resulting appearance would be undesirable.

Second, the prolonged presence of the guard petals 4 due to the constricting action of the netting sleeve 2 results in the reduction in the amount of ambient light reaching the inner petals 5 of the rose head 3 during the final growth stage. Since the guard petals 4 would normally block light from reaching the inner petals 5, there is less light and therefore less heat incident on the inside of the rose head. As a result, the temperature of the rose head is reduced, which in turn acts to reduce the respiration rate. The reduced respiration rate decreases the amount of energy consumed, which in turn decreases the amount of carbohydrates expended by the flower for respiration. The result of this process is that the rose head becomes stronger and healthier and grows to an increased size, without the guard petals opening because the carbohydrate content within the flower is retained in the head due to the lower respiration. The result is a higher rate of growth of the rose head in the same growing time as a plant without the use of the netting.

The timing of the placement of the nylon netting sleeve over the rose head is critical to the present invention. If the netting sleeve is placed over the rose head too soon prior to the cutting stage, the rose will tend to accumulate too much water on the head and may develop water rot, or botrytis. This results from the rose petals being held too closely together and not allowing enough evaporation on the petal surface while trapping in existing moisture. In addition, early usage of the netting sleeve prevents light interception by most of the rose head. Since during the initial stages of growth, rosebuds need light to build color pigments, then early blockage of light would negatively affect this process. On the other hand, if the netting sleeve is placed over the rose head too close to the cutting stage, there is no increase in rose head size, and the advantages presented by the use of the instant invention are not achieved because the guard petals open in the normal course of growth.

The optimal time for sleeve placement on the rose head has been determined to vary according to the particular variety of rose being grown. Table A below lists the experimentally determined optimal number of days prior to the normal cutting time of the rose stem that the sleeve should be placed on the rose head.

TABLE A

| Variety | Number of days prior to normal cutting time |
| --- | --- |
| Vivaldi, Osiana, Marlyse, Livia, Jacaranda | 2 |
| Sonia, Aalsmeer Gold, Slyline, Confetti, Pailene, Lomada, Lorena, Lovely Girl, Ariamna, Harmony, Blue Bird, Parao, Diplomat, Lasser, Anna, Prive | 3–5 |
| Carolla, Madame Delbard, Dallas, First Red | 5–7 |

Figure 3A:
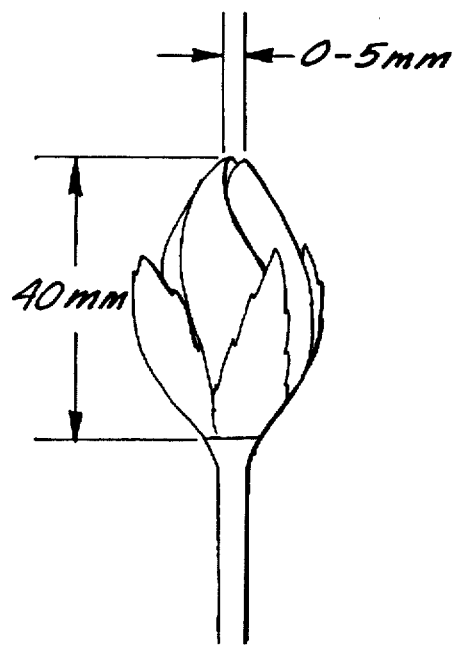
FIGS. 3A through 3D depict the final growth stages of a rose head.
Figure 3B:
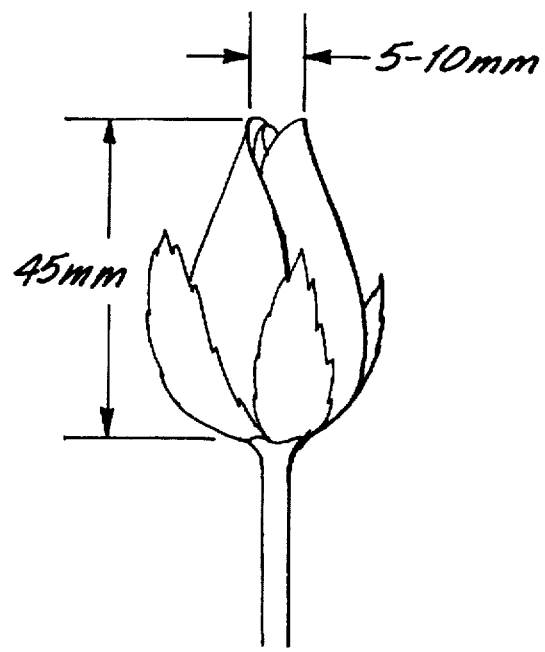
Figure 3C:
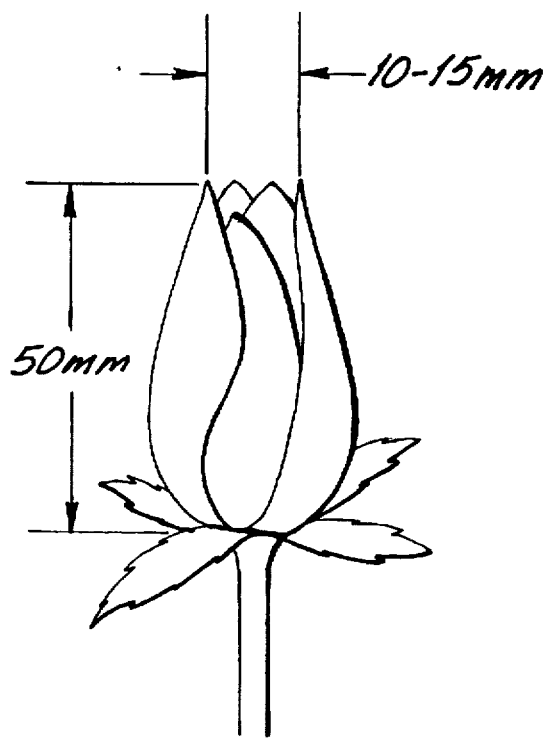
Figure 3D:
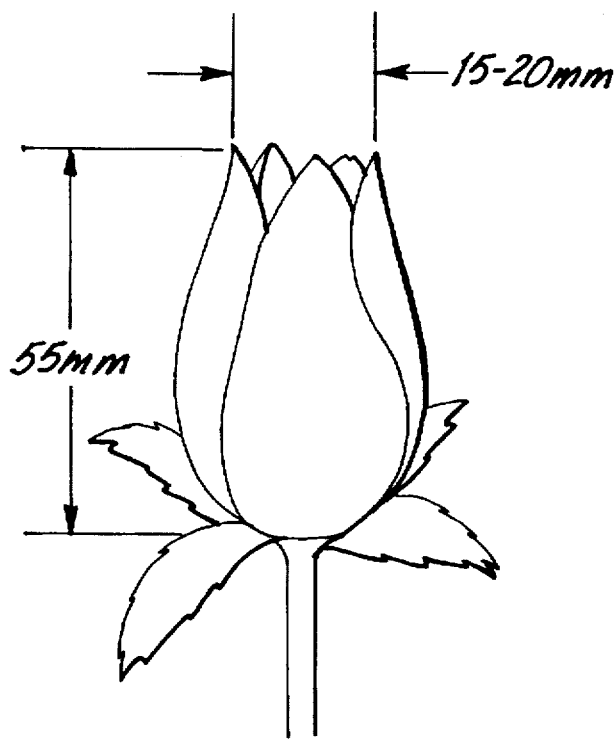

FIGS. 3A through 3D illustrate the various progressive growth stages of a normal rose head. The time between the stages varies, but it is approximately several days. In the normal case, the rose should be cut from the plant at the stage in FIG. 3C in order to achieve optimal head size and shelf life after cutting. If the cutting of the rose head is delayed until the stage shown in FIG. 3D, the rose is overdeveloped and the shelf life is severely shortened due to the opening of the petals. When the netting sleeve of the present invention is placed on the rose head as described herein, then the head will grow approximately to the size as shown in FIG. 3D while maintaining the petal tightness shown in FIG. 3C. Thus, by implementing the present invention, the larger head size is achieved while maintaining the petals in relative tightness and keeping the optimal shelf life intact after cutting.

Although the present invention has been described herein with reference to the use of a nylon netting, it is noted that other materials which give the desired properties of elasticity and resiliency may be also used within the spirit and scope of the claims presented below. For example, an elastic or rubber material may be used to constrict the outer petals from opening. In addition, the present invention may be applied to other flowers which may have a similar growth and cutting cycle in order to obtain larger flowers with a longer shelf life than has been otherwise obtainable. Further, the number of days for keeping the sleeve on the head prior to cutting may be varied as required by the particular flower variety, climate conditions, and requirements of the grower while still operating within the scope of the present invention as claimed herein.

I claim:

1. A method for increasing the size of a rose head prior to cutting the rose head from its plant comprising at least partially preventing the rose head from opening prior to cutting the rose head from the plant, wherein the rose head is at least partially prevented from opening by constricting the rose head with an elastic material wrapped around the rose head, wherein the elastic material is a netting sleeve having at least one open end suitable for placing over the rose head, the netting sleeve being comprised of an elastic netting material capable of stretching so as to fit snugly over the rose head.

2. The method of claim 1 wherein said elastic netting material is comprised of nylon.

3. The method of claim 1 wherein said elastic netting material is comprised of rubber.

4. The method of claim 1 wherein the rose head is at least partially constricted for a predetermined time period prior to cutting from the plant.

5. A method for increasing the size of a rose head prior to cutting the rose head from its plant comprising wrapping an elastic netting material substantially around the rose head, the elastic netting material making substantial contact with said rose head so as to constrict the opening of said rose head.

6. The method of claim 5 wherein said elastic netting material is comprised of nylon.

7. The method of claim 5 wherein said elastic netting material is comprised of rubber.

8. The method of claim 5 wherein the elastic netting material is placed over the rose head for a predetermined time period prior to cutting from the plant.

* * * * *